(12) United States Patent  (10) Patent No.: US 8,113,729 B2
Solan  (45) Date of Patent: Feb. 14, 2012

(54) TOOTHPASTE DROPLETS

(75) Inventor: Wayne R. Solan, Fort Lauderdale, FL (US)

(73) Assignee: Dental Development Systems, LLC, Ft. Lauderdale, FL (US)

(*) Notice: Subject to any disclaimer, the term of this patent is extended or adjusted under 35 U.S.C. 154(b) by 19 days.

(21) Appl. No.: 12/499,532

(22) Filed: Jul. 8, 2009

(65) Prior Publication Data

US 2011/0008094 A1 Jan. 13, 2011

(51) Int. Cl.
  *B43K 5/14* (2006.01)
(52) U.S. Cl. ........................................ 401/132
(58) Field of Classification Search .......... 401/132, 401/133; 424/49
  See application file for complete search history.

(56) References Cited

U.S. PATENT DOCUMENTS

| | | | |
|---|---|---|---|
| 1,411,681 A | | 4/1922 | Burlew |
| 2,004,957 A | | 4/1934 | Messner |
| 1,995,374 A | | 3/1935 | Young |
| 2,778,045 A | * | 1/1957 | Bly et al. ................. 401/132 |
| 4,292,304 A | | 9/1981 | Barels et al. |
| D314,441 S | | 2/1991 | Greither |
| D373,188 S | | 8/1996 | Williams |
| D377,684 S | | 1/1997 | Schurig et al. |
| D411,296 S | | 6/1999 | Waymel |
| D457,948 S | | 5/2002 | Meron et al. |
| 6,524,023 B2 | | 2/2003 | Andersen |
| 6,845,883 B2 | | 1/2005 | Pieri |
| 7,074,390 B2 | | 7/2006 | MacKinnon |
| 7,287,643 B1 | | 10/2007 | Glover, Sr. |
| 7,338,664 B2 | | 3/2008 | Tseng et al. |
| 7,478,959 B2 | | 1/2009 | Hohlbein |
| 2004/0091431 A1 | * | 5/2004 | Alexander ................ 424/49 |
| 2004/0185011 A1 | | 9/2004 | Alexander et al. |
| 2005/0260141 A1 | | 11/2005 | Alexander et al. |
| 2007/0231425 A1 | * | 10/2007 | Ream et al. ................ 426/3 |
| 2008/0014010 A1 | | 1/2008 | Bartschi et al. |
| 2008/0038046 A1 | | 2/2008 | Jalili |
| 2009/0044356 A1 | | 2/2009 | Noble et al. |

FOREIGN PATENT DOCUMENTS

WO 0226078 A3 4/2002

OTHER PUBLICATIONS

Happi.com; "Accessorize your smile"; www.happi.com/articles/2009/02/accessorize-your-smile; last visited on Jul. 8, 2009.

* cited by examiner

*Primary Examiner* — Gregory Huson
*Assistant Examiner* — Jennifer C Chiang
(74) *Attorney, Agent, or Firm* — Adam C. Underwood, Esq.; Carey, Rodriquez, Greenberg & O'Keefe

(57) ABSTRACT

A device, method, and system for delivering toothpaste to a user. In one embodiment of the invention, a droplet for delivering toothpaste to a user can be provided. The droplet can include a dissolvable outer membrane defining a volume with toothpaste inside the volume. The outer membrane can include a tail portion, which is configured to be embedded into the bristles of a toothbrush. The droplet further can include one or more extensions coupled to the outer surface of the outer membrane, the one or more extensions can have a triangular shape, a barb shape or the like. In one aspect of this embodiment, the droplet further can include a logo, a cartoon character, a word or the like printed on the outer membrane.

6 Claims, 5 Drawing Sheets

TOOTHPASTE DROPLETS

BACKGROUND OF THE INVENTION

1. Field of the Invention

The field of the invention generally relates to toothpaste and more particularly to a droplet of toothpaste configured to be embedded into the bristles of a toothbrush.

2. Description of the Related Art

People are encouraged to use toothpaste at least twice daily and believe that toothpaste is a completely safe health care product. Most toothpaste contains fluoride because fluoride helps to prevent dental cavities and dental decay. Fluoride, however, can cause health risks as well. For example, poisoning may occur following excessive ingestion of a fluoride-containing product such as toothpaste. In 1997, the Food & Drug Administration (FDA) started to require a warning on toothpastes containing fluoride. The FDA warning cautions users "If you accidentally swallow more than used for brushing, seek professional help or contact a poison control center immediately". In 2006, the American Association of Poison Control Centers (AAPCC) reported 22,168 exposures involving toothpaste with fluoride and in 2007 the AAPCC reported 24,237 exposures involving toothpaste with fluoride (AAPCC Annual Reports available on the website www.aapcc.org). In other cases, the toxic effects following ingestion of toothpaste can result in gastrointestinal discomfort, e.g., severe stomachaches and diarrhea. Moreover, the ingestion of fluoride can cause a discoloration of the teeth called dental fluorosis. Fluoride produces dental fluorosis by damaging the cells that produce the tooth's enamel during formation of the tooth. Dental fluorosis appears as a range of cosmetic changes varying from white spots on the teeth to brown stains. In severe cases, the teeth are pitted and fragile.

The risk of excessive ingestion of toothpaste is not prevented by the traditional tubes of toothpaste. Traditional tubes and pumps do not provide users with an appropriate quantity of toothpaste on their toothbrush. Thus, the amount of toothpaste used for brushing cannot be determined nor controlled. In addition to the health risks due to ingestion of toothpaste, the traditional tubes present other disadvantages. For example, traditional tubes frequently cause waste and mess of toothpaste. In addition, there is an environmental cost due to the number of empty toothpaste tubes as these traditional tubes require an extended time period to degrade.

One attempt to resolve these issues included providing a single use chewable capsule containing toothpaste and/or toothbrush kit with a means for receiving a capsule of toothpaste. However, the risk of swallowing capsules of toothpaste still exists insofar as the capsules cannot hold onto the brush and the toothbrush kit includes a toothpaste delivery system that requires some adaptation to retain the capsules of toothpaste.

BRIEF SUMMARY OF THE INVENTION

Embodiments of the present invention address deficiencies of the art in respect to delivery of toothpaste and provide a novel and non-obvious device, method, and system for delivering toothpaste to a user. In one embodiment of the invention, a droplet for delivering toothpaste to a user can be provided. The droplet can include a dissolvable outer membrane defining a volume with toothpaste inside the volume. The outer membrane can include a tail portion, which is configured to be embedded into the bristles of a toothbrush. The droplet further can include one or more extensions coupled to the outer surface of the outer membrane, the one or more extensions can have a triangular shape, a barb shape or the like. In one aspect of this embodiment, the droplet further can include a logo, a cartoon character, a word or the like printed on the outer membrane.

In another embodiment of the invention, a method for cleaning teeth can be provided. The method can include providing a droplet that can have a dissolvable outer membrane that defines a volume with toothpaste inside the volume. The outer membrane can include a tail portion, which is configured to be embedded into the bristles of a toothbrush. The provided droplet further can include one or more extensions coupled to the outer surface of the outer membrane where the one or more extensions can have a triangular shape, a barb shape or the like. In one aspect of this embodiment, the droplet further can include a logo, a cartoon character, a word or the like printed on the outer membrane. The method can further include placing the droplet into the bristles of the toothbrush, releasing the toothpaste from the outer membrane into the bristles of the toothbrush and cleaning the teeth with the toothpaste. In an aspect of this method, the release of toothpaste can include dissolving the dissolvable outer membrane with saliva. In another aspect of this method, the method can include swallowing the dissolvable outer membrane. In yet another aspect of this method, the outer surface of the tail section of the outer membrane can include one or more extensions.

In yet another embodiment of the invention, a container for dispensing droplets of toothpaste can be provided. The container can include a shell body with a top and a bottom, the bottom opposite the top and a spout rotabably connected to the top and configured to release the droplets of toothpaste.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
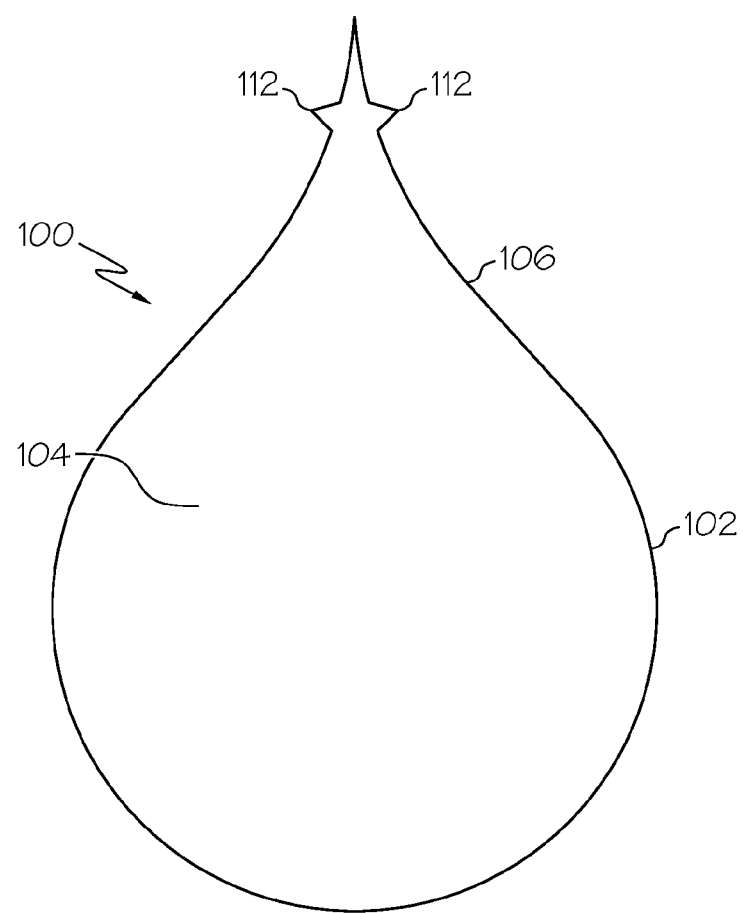
FIG. 1 is a front view of a droplet of toothpaste made in accordance with the present invention.

Each droplet of toothpaste contains the recommended amount of toothpaste for a single cleaning of the teeth of the user. Waste can be eliminated by providing the consumer with exactly the amount of toothpaste necessary to brush their teeth. The droplets can be contained and delivered in a sealed plastic pack and that pack can be filled with the recommended number of droplets to provide the brushing desired. For example, a pack of two droplets (enough for one day's brushing) can be supplied by hotels, airlines, companies, hospitals and prisons to the residents, passengers, employees, patients and inmates to provide the recommended amount of toothpaste for their stay. This convenient delivery system of toothpaste eliminates significant waste. The droplets of toothpaste also are very convenient for travel because they are easy to carry, pass easily through security in airports and the droplets do not require as much space and weight as traditional toothpaste tubes.

In embodiments, the toothpaste droplets can have a teardrop shape. The toothpaste droplets are configured to be embedded into the bristles of the toothbrush. The user only needs to place a droplet on the bristles of a toothbrush and the droplet can stick to the toothbrush with no additional help. The droplets do not need to be pressed or squeezed into the toothbrush in order to be held by the bristles. In embodiments, depending on the type of toothbrush and/or bristles, a slight amount of pressure may be required to embed the droplet into the bristles but typically no pressure is required. In addition, the droplets do not fall out and avoid being accidentally swallowed when a user brings the toothbrush into his/her mouth. Generally speaking, the risk of ingestion of toothpaste is higher with children. Indeed, as most children have not learned to control the swallowing reflex, they can very easily swallow toothpaste placed in their mouth. Furthermore, children also can swallow toothpaste deliberately when they like its taste and frequently toothpaste for kids can have different flavors, colors or compositions to appeal and motivate the children to brush their teeth. The risk of swallowing is prevented by the tear-shaped droplets of toothpaste that remain embedded into the bristles of the toothbrush.

The droplets are wrapped with a dissolvable film strip. Thus, the toothpaste contained into the droplets spreads over the toothbrush when water is poured on the droplets. A droplet does not need to be squeezed or crushed and chewed to release the toothpaste in it. Thus, the droplet keeps the brushing process easy and tidy as the user can place the droplet onto the toothbrush, can wet the droplet with water or saliva and can brush the user's teeth. Although the term toothpaste is used throughout this specification, the term toothpaste is meant to include various types of dentifrice, for example, the term toothpaste can include a paste, liquid, gel or powder used to maintain good oral hygiene.

Tear-shaped droplets of toothpaste can retain a hold on all kinds of bristles or toothbrushes. The toothbrush does not need to be specifically designed to retain the droplets nor do the bristles have to be arranged for reception of the droplets. Accordingly, an economic advantage is realized since good health care includes the frequent replacement of toothbrushes and the tear-shaped droplets of toothpaste can be used with any toothbrush. For example, the tear-shaped droplets of toothpaste fit nicely onto rotatable or spinning toothbrushes. In addition, the droplets are easy to use which is greatly appreciated especially by kids and seniors who may have some difficulties with a tube of toothpaste or a toothbrush kit that has a complicated toothpaste delivery system.

Accordingly, this invention has developed an economical and easy way to use droplets of toothpaste to address the health risks related to excessive ingestion of toothpaste by a user. In illustration, FIG. 1 depicts a droplet of toothpaste 100. As shown in FIG. 1, a droplet of toothpaste 100 can include an outer membrane 102 and a certain amount of toothpaste 104 inside. In embodiments, the outer membrane 102 can be formed by use of containment materials. The containment materials can be made of dissolvable film strip technology such as poly vinyl alcohol which dissolves in the presence of water or saliva. Alternatively, in embodiments, the containment materials can be made of an edible film, such as cellulose, carrageen, starch and gelatin.

In embodiments, the membrane 102 can be printed with logos, characters and the like, depending on the targeted consumers, e.g., children, adults and seniors. Different formulations of toothpaste 104 can be enclosed in the membrane 102. Each droplet 100 can contain the recommended amount of toothpaste prescribed by the American Dental Association (ADA) to clean the teeth of the user one time.

A pre-measured amount of toothpaste can be determined based on the need of the users. For most children, teething begins by six months age and the brushing of the child's teeth is required during the life of the teeth. However, the necessary amount of toothpaste to properly brush one's teeth can differ depending of the age of the user. For example, a pea-sized amount, e.g., 0.8 to 1.2 grams of toothpaste is recommended for the teeth of toddlers. In contrast, one and one half to twice the pea-sized amount, e.g., 1.2 to 1.8 grams of toothpaste is recommended for kids who have a full set of baby teeth. Moreover, the droplet 100 can provide different quantities of toothpaste adapted to the need of the users e.g., the recommended amount for adults is 1.6 to 2.4 grams. Furthermore, the packaging of the droplets of toothpaste can be adapted to targeted consumers and/or providers. As each droplet 100 contains the recommended amount of toothpaste for one complete brushing of the teeth of a user and brushing twice a day is the recommended frequency, the packaging of the droplets can contain the recommended quantity of toothpaste for a determined period of time. For example, some potential providers of toothpaste such as hotels or airline companies are able to foresee the number of days their clients planned to stay and thus the quantity of droplets of toothpaste they want to offer to each client. Other potential providers of toothpaste like hospitals or prisons can be interested in this healthy and economical delivery system of toothpaste.

Figure 2:
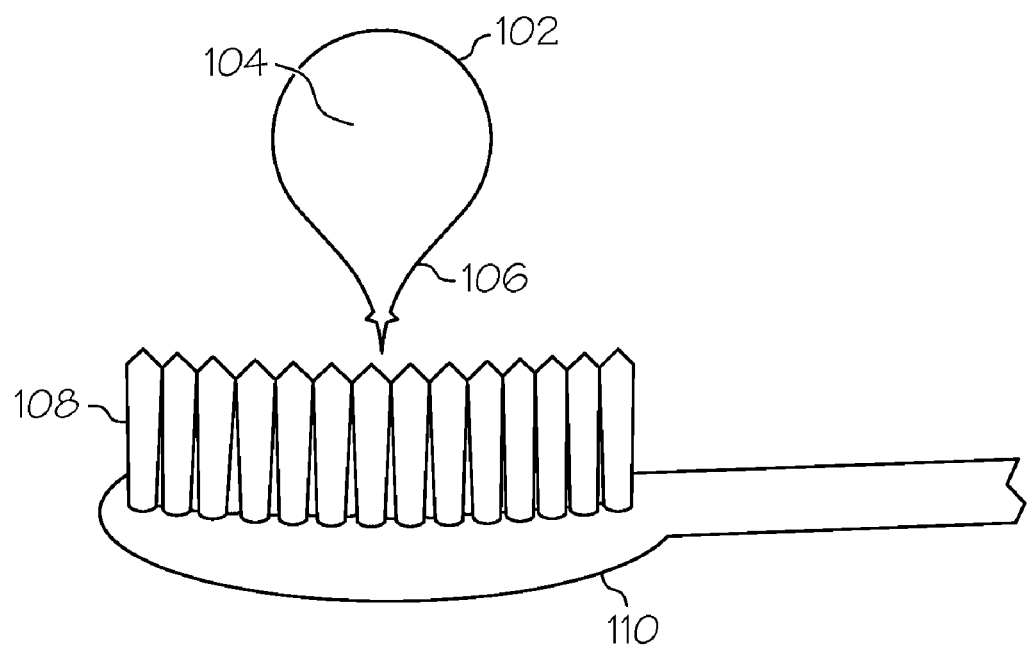
FIG. 2 is a front view of the droplet of toothpaste positioned for embedding onto a toothbrush.
Figure 3:
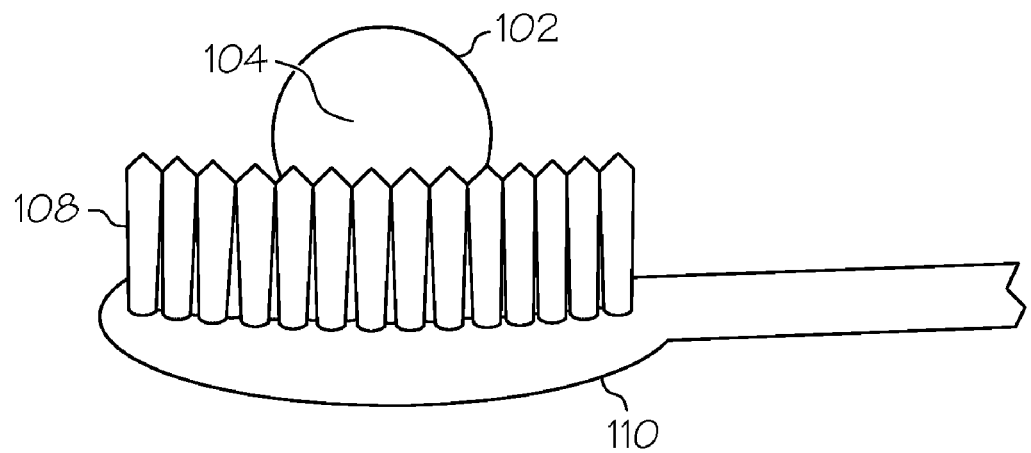
FIG. 3 is a front view of the droplet embedded into bristles of a toothbrush.

As shown in FIGS. 2 and 3, the droplet 100 can be shaped as a teardrop and can include a tail portion 106 that can be easily embedded into the bristles 108 of a toothbrush 110. The droplet 100 can stick in the bristles 108 so that the droplet 100 does not fall off when the toothbrush 110 is brought into the mouth. The outer membrane 102 of the toothpaste droplet 100 can dissolve once it comes in contact with water or saliva. To activate the droplet 100, a consumer can choose either to pour water on the droplet 100 while the droplet 100 is embedded into the bristles of the toothbrush 110 or to wet the droplet 100 with saliva while the droplet 100 is embedded into the bristles. In any case, the risk of swallowing is prevented insofar as the bristles of the toothbrush retain the droplet 100 of toothpaste and allows the toothpaste 104 to spread through the bristles 108 of the toothbrush 110 once the outer membrane 102 is dissolved.

Figure 6:
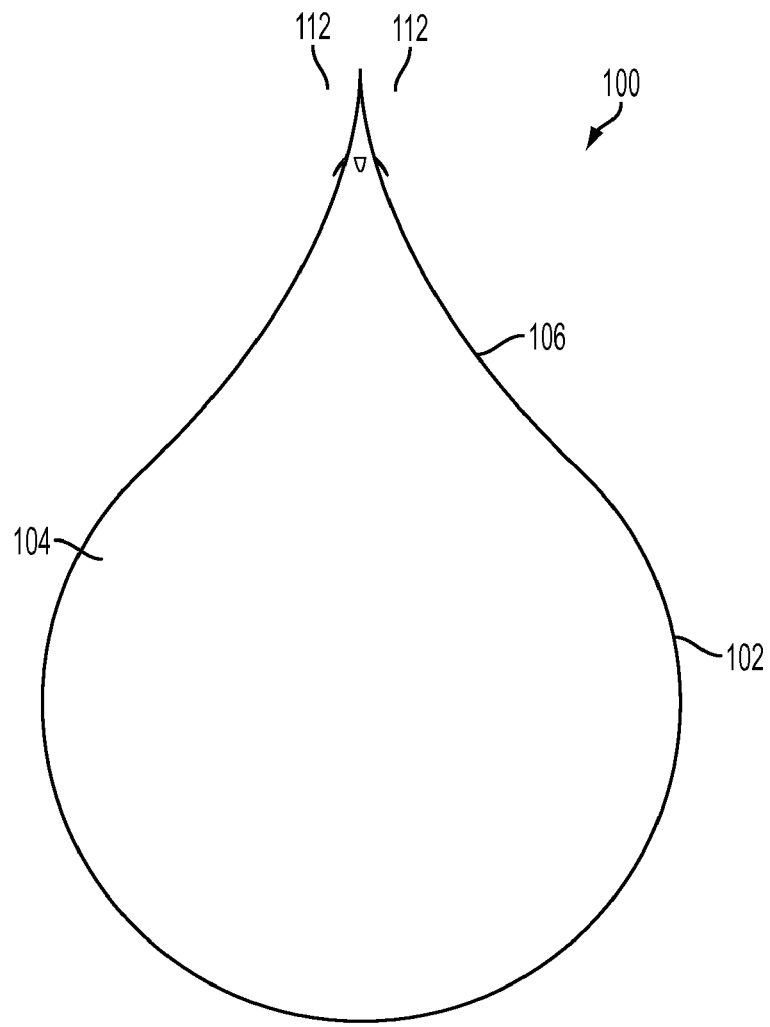
FIG. 6 is a front view of another droplet of toothpaste made in accordance with the present invention.

In embodiments, the tail portion 106 of the toothpaste droplet 100 can include one or more extensions 112 protruding from the outer surface of tail portion 106 that form irregularities on the outer surface of the tail portion 106 of the outer membrane 102 to anchor into the bristles 108 of a toothbrush 110. For example, the extensions 112 can be one or more triangular-shaped protrusions, rounded protrusions, rounded barbs (best illustrated in FIG. 6) or the like. In embodiments, the extensions 112 can be positioned in a row, e.g., inline or can be scattered about the outer surface of tail portion 106.

Regardless of the shape of the extensions 112, these extensions 112 are configured to aid in attaching or embedding the tail portion 106 of the toothpaste droplet 100 into the bristles 108 of the toothbrush 110. In embodiments, the toothpaste droplet 100 can have a teardrop shape, diamond shape, e.g., an emperor's cut, or a similar shape.

Figure 4:
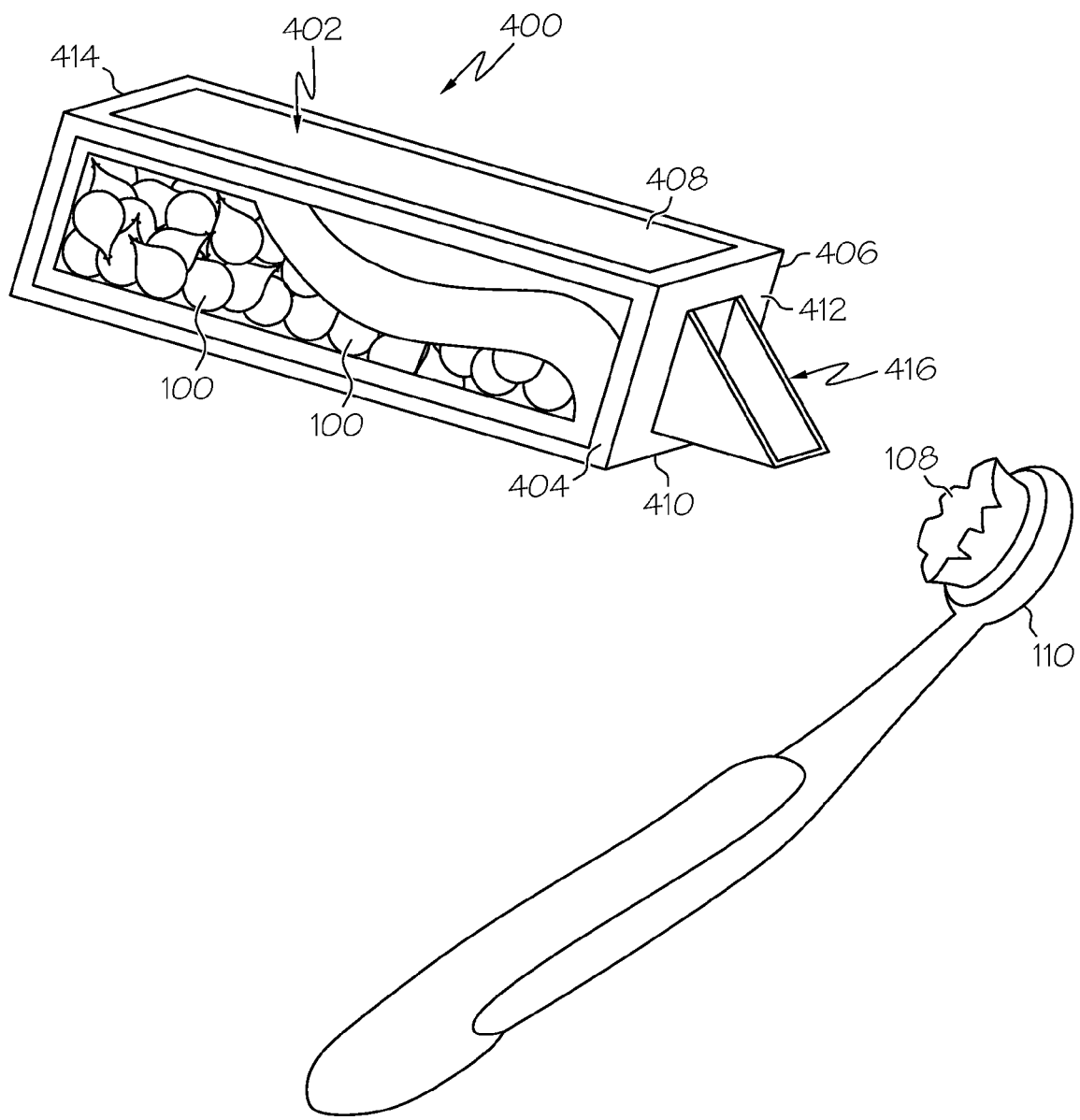
FIG. 4 is a perspective view of a container for dispensing a droplet of toothpaste made in accordance with one embodiment of the present invention; and, FIG. 5 is a perspective view of another container for dispensing a droplet of toothpaste made in accordance with one embodiment of the present invention.

Several types of packaging are available to store and dispense the toothpaste droplets 100. As illustrated in FIG. 4, a container 400 in the form of a tube or box can be provided to store and dispense the toothpaste droplets 100. Container 400 can have a shell body 402 that can be shaped to form a box-like structure. The box-like structure can have four sides 404, 406, 408, 410, a top 412 and a bottom 414 opposite the top 412. The container 400 further can include a spout 416 for dispensing the toothpaste droplets 100. The spout 416 can be located in the top 412, the bottom 414 or one of the sides 404, 406, 408, 410. In embodiments, the spout 416 can be activated by lifting a distal edge, e.g., the end furthest from the middle of the middle of the top 412 section, of the spout 416. In embodiments, container 400 can include a liner (not shown) that can contain the toothpaste droplets 100. The liner can be placed within the shell body 402. The liner can be made of various plastic materials including biodegradable plastic. Although FIG. 4 illustrates the container 400 as a box-like structure, container 400 is not limited to this shape. Instead it is expected that container 400 can take numerous shapes such as a tube, a cylinder and the like.

Figure 5:
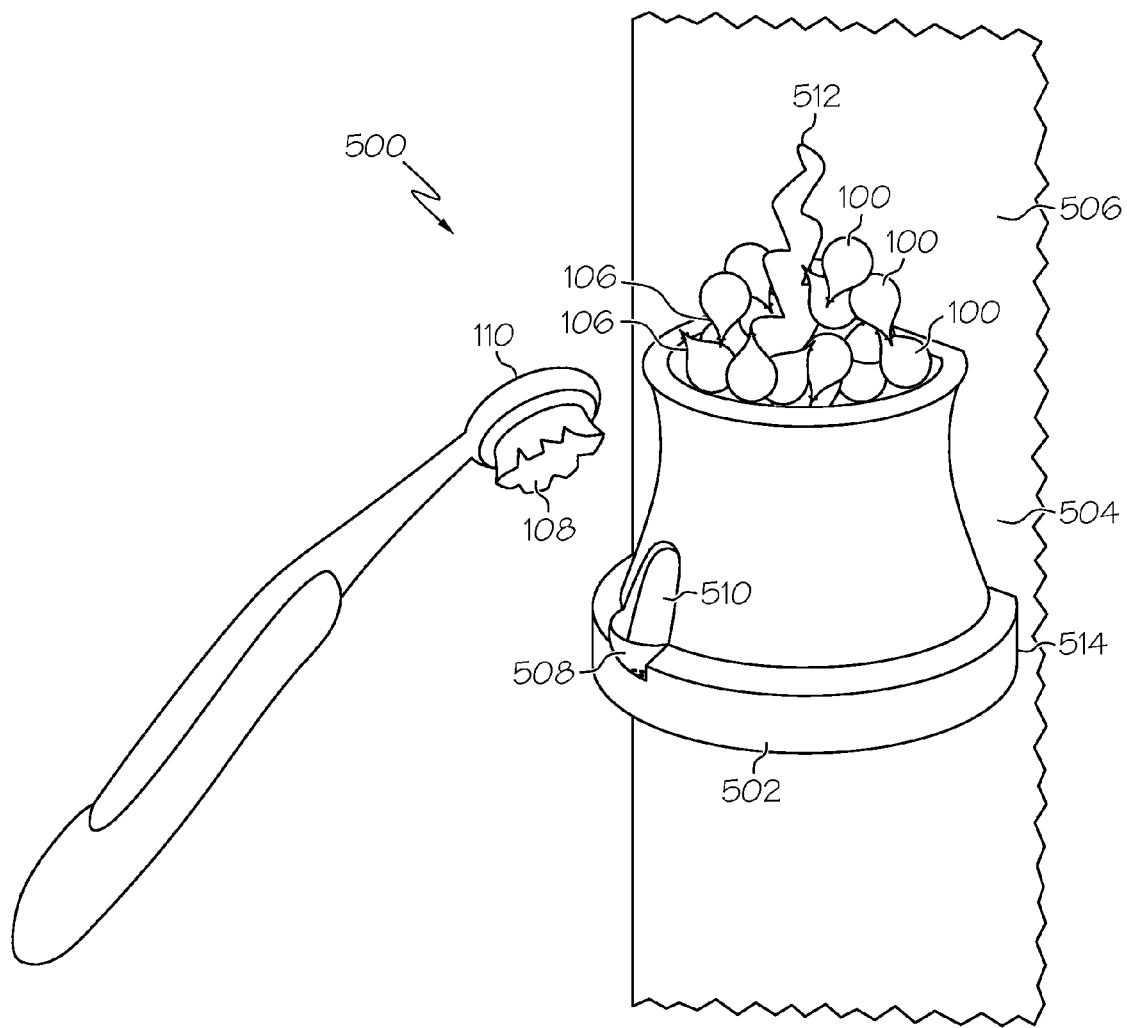

As illustrated in FIG. 5, a container 500 in the form of a gumball dispenser can be provided to store and dispense the toothpaste droplets 100. The container 500 can have a shell body 502 that can be shaped to form a bottom portion of a gumball like dispenser. For example, shell body 502 can include a bottom or base 504, a side portion 514, a dome 506, a guide spiral 512, a dispensing slot 510 and a retaining wall 508. In embodiments, the guide spiral 512 can be fixed or rotatable. The dome can include a liner (not shown) that can contain the toothpaste droplets 100.

In embodiments, the toothpaste droplet 100 can be used in a method for brushing the teeth of a user. For example, first a droplet of toothpaste can be provided. The droplet can include a dissolvable outer membrane that defines a volume where toothpaste fills the defined volume. The outer membrane also can include a tail portion that is configured to embed into bristles of a toothbrush. Next the provided droplet can be placed onto the bristles of the toothbrush. At this point, the toothpaste can be released from the outer membrane into the bristles of the toothbrush by wetting the droplet with water or saliva. Finally the teeth can be cleaned with the toothpaste. In embodiments, the outer membrane 102 of the droplet 100 can be formed from a dissolvable film strip technology. In embodiments, the outer surface of the tail section of the outer membrane can have one or more extensions. These extensions can have various shapes, including but not limited to, a triangular shape or a barb shape. In addition, the outer membrane of the droplet can from a teardrop shape.

The invention has been described with respect to certain preferred embodiments, but the invention is not limited only to the particular constructions disclosed and shown in the drawings as examples, and also comprises the subject matter and such reasonable modifications or equivalents as are encompassed within the scope of the appended claims.

What is claimed is:

1. A droplet comprising:
 a dissolvable outer membrane defining a volume; and,
 toothpaste inside the volume;
 wherein the outer membrane includes a tail portion, the tail portion being configured to embed into bristles of a toothbrush;
 wherein the outer membrane is formed from a dissolvable film strip; and,
 a plurality of extensions forming irregularities on the outer surface of the tail section of the outer membrane.

2. The droplet of claim 1, wherein the plurality of extensions have a triangular shape.

3. The droplet of claim 1, wherein the plurality of extensions have a barb shape.

4. The droplet of claim 1, wherein the outer membrane forms a teardrop shape.

5. The droplet of claim 1, wherein the outer membrane includes one of a logo, a cartoon character and a word.

6. The droplet of claim 1, wherein the dissolvable film strip is polyvinyl alcohol.

* * * * *